United States Patent
Lai et al.

(10) Patent No.: US 9,766,218 B2
(45) Date of Patent: Sep. 19, 2017

(54) GAS CURTAIN AT INLET FOR TRACE DETECTORS

(71) Applicant: Morpho Detection, LLC, Newark, CA (US)

(72) Inventors: Hanh Lai, Arlington, MA (US); Bradley Douglas Shaw, Plaistow, NH (US); Hartwig Schmidt, Reading, MA (US); Stephen Davila, Beverly, MA (US); Robert Michalczyk, Dracut, MA (US)

(73) Assignee: Morpho Detection, LLC, Newark, CA (US)

( * ) Notice: Subject to any disclaimer, the term of this patent is extended or adjusted under 35 U.S.C. 154(b) by 172 days.

(21) Appl. No.: 14/530,081

(22) Filed: Oct. 31, 2014

(65) Prior Publication Data

US 2016/0123942 A1    May 5, 2016

(51) Int. Cl.
| | | |
|---|---|---|
| *G01N 1/22* | (2006.01) | |
| *G01N 33/00* | (2006.01) | |
| *G01N 1/44* | (2006.01) | |
| *G01N 1/24* | (2006.01) | |

(52) U.S. Cl.
CPC ........... *G01N 33/0011* (2013.01); *G01N 1/44* (2013.01); *G01N 33/0021* (2013.01); *G01N 1/22* (2013.01); *G01N 1/2258* (2013.01); *G01N 1/24* (2013.01); *G01N 2001/2261* (2013.01); *G01N 2001/2282* (2013.01)

(58) Field of Classification Search
CPC .......................................................... G01N 1/22
USPC ....................................................... 73/863.11
See application file for complete search history.

(56) References Cited

U.S. PATENT DOCUMENTS

| | | | | |
|---|---|---|---|---|
| 3,824,167 A | * | 7/1974 | Oswin et al. ............ | G01N 1/34 204/411 |
| 4,023,398 A | | 5/1977 | French et al. | |
| 4,121,099 A | | 10/1978 | French et al. | |
| 4,551,624 A | * | 11/1985 | Spangler ............... | G01N 27/622 250/282 |
| 4,819,477 A | | 4/1989 | Fisher et al. | |
| 4,987,767 A | * | 1/1991 | Corrigan ............... | G01N 1/2214 250/282 |
| 5,032,721 A | * | 7/1991 | Bacon ................... | G01N 27/622 250/282 |

(Continued)

FOREIGN PATENT DOCUMENTS

| | | | | |
|---|---|---|---|---|
| EP | WO2013171571 | * | 11/2013 | ............ G01N 27/62 |
| EP | 3015858 A1 | * | 10/2015 | ............ G01N 33/00 |

OTHER PUBLICATIONS

Richard Sleeman, 'Rapid Screening of banknotes for the presence of controlled substances by thermal desorption atmospheric pressure chemical ionisation tandem mass spectrometry', 1999, The Analyst 124, 103-108.*

(Continued)

*Primary Examiner* — Clayton E Laballe
*Assistant Examiner* — Kevin Butler
(74) *Attorney, Agent, or Firm* — Armstrong Teasdale LLP

(57) ABSTRACT

The present disclosure is directed to methods and systems for creating a gas curtain inlet for a detector of a substance of interest. The methods and systems include introducing a carrier gas into an inlet to block out atmospheric air without having to make the inlet a sealed system.

18 Claims, 8 Drawing Sheets

(56) References Cited

U.S. PATENT DOCUMENTS

| | | | | |
|---|---|---|---|---|
| 5,095,206 A | * | 3/1992 | Bacon, Jr. | H01J 47/008 250/282 |
| 5,109,691 A | * | 5/1992 | Corrigan | G01N 1/2214 250/286 |
| 5,162,652 A | * | 11/1992 | Cohen | G01N 1/2214 250/288 |
| 5,192,865 A | * | 3/1993 | Zhu | H01J 49/105 250/281 |
| 5,234,838 A | * | 8/1993 | Bacon, Jr. | G01N 27/622 250/282 |
| 5,338,931 A | * | 8/1994 | Spangler | H01J 49/162 250/287 |
| 5,345,809 A | * | 9/1994 | Corrigan | G01N 1/2214 250/286 |
| 5,405,781 A | * | 4/1995 | Davies | G01N 27/622 250/282 |
| 5,491,337 A | | 2/1996 | Jenkins et al. | |
| 6,192,766 B1 | | 2/2001 | Gardhagen et al. | |
| 6,446,514 B1 | * | 9/2002 | Danylewych-May | G01N 1/02 73/863.12 |
| 6,642,513 B1 | | 11/2003 | Jenkins et al. | |
| 6,708,572 B2 | | 3/2004 | Jenkins et al. | |
| 6,774,360 B2 | * | 8/2004 | Guevremont | H01J 49/004 250/281 |
| 6,978,657 B1 | | 12/2005 | Baumann et al. | |
| 7,067,818 B2 | * | 6/2006 | Harrison | G01J 3/2803 250/372 |
| 7,312,444 B1 | * | 12/2007 | Willougbhy | H01J 49/065 250/288 |
| 7,377,188 B2 | | 5/2008 | Jenkins | |
| 7,714,282 B2 | | 5/2010 | Guevremont et al. | |
| 7,902,501 B2 | | 3/2011 | Landgraf et al. | |
| 8,047,053 B2 | * | 11/2011 | Call | G01N 1/2202 73/28.01 |
| 8,245,564 B1 | * | 8/2012 | Ewing | G01N 1/22 73/31.02 |
| 9,134,273 B2 | * | 9/2015 | LeBlanc | H01J 49/00 |
| 2002/0148974 A1 | * | 10/2002 | Hung | G01N 30/00 250/443.1 |
| 2005/0085740 A1 | * | 4/2005 | Davis | A61B 5/08 600/532 |
| 2007/0034024 A1 | * | 2/2007 | Syage | G01N 1/2205 73/863.12 |
| 2008/0250877 A1 | * | 10/2008 | Wu | G01N 1/14 73/864.33 |
| 2009/0032701 A1 | * | 2/2009 | Rodier | G01N 27/622 250/282 |
| 2011/0068264 A1 | * | 3/2011 | Xu | G01N 27/622 250/286 |
| 2011/0174966 A1 | | 7/2011 | Wollnik et al. | |
| 2011/0247494 A1 | * | 10/2011 | Dinnage | B01D 53/1456 95/92 |
| 2014/0117223 A1 | * | 5/2014 | Stott | H01J 49/0459 250/282 |
| 2015/0300927 A1 | * | 10/2015 | Easton | G01N 27/622 73/863.52 |
| 2015/0340214 A1 | * | 11/2015 | Wu | H01J 49/049 250/282 |
| 2016/0123942 A1 | * | 5/2016 | Lai | G01N 1/44 73/863.11 |

OTHER PUBLICATIONS

European Search Report, 'EP15003073', Dec. 21, 2015, Munich.*
European Patent Office, European Search Report EP15003073, Jan. 22, 2016, 13 pages.*
Sleeman et al, Rapid screening of banknotes for the presence of controlled substances by thermal desorption atmospheric pressure chemical inonisation tandem mass spectrometry, The Analyst, 1999, pp. 124, 103-108.*
Extended European Search Report, Application No. 15003073.2, dated Jan. 22, 2016, pp. 13.
Sleeman et al., Rapid screening of banknotes for the presence of controlled substances by thermal desorption atmosphere pressure chemical ionisation tandem mass spectrometry, The Analyst, dated Jan. 1, 1999, vol. 124, No. 2, pp. 103-108.

* cited by examiner

GAS CURTAIN AT INLET FOR TRACE DETECTORS

BACKGROUND OF THE DISCLOSURE

The embodiments described herein relate generally to methods and systems for creating a gas curtain inlet for a detector of a substance of interest.

Over the past several decades, various field analytical technologies have been developed for the detection of substances of interest, such as explosives and illicit drugs. One exemplary issue with the efficacy of these technologies is that atmospheric air in the environment can be highly contaminated with potential interferants or contain high moisture levels where detectors, such as trace detectors, are used. Examples of such environments are air cargo facilities, sea ports, battle fields, and cities with poor air quality index.

Most trace detectors perform at an optimal level (i.e., good sensitivity and selectivity) when they are free of contaminated and/or moist gas introduced from the environment. Contaminants and/or moist gas can suppress signal responses for reactant ion peaks (RIP) or generate signals that interfere with detection windows. Additionally, when contaminants and/or moisture from the environment are introduced into the system, a longer amount of time is required for the system to re-establish a steady state chemistry, which lowers the system's throughput.

The present disclosure overcomes the deficiencies of the prior art by creating a cleaned, dried and/or doped air into an inlet of a detector and blocking out atmospheric air without having to make the inlet a sealed system.

BRIEF DESCRIPTION OF THE DISCLOSURE

In one aspect of the present disclosure, a method of creating a gas curtain at an inlet for a detector of a substance of interest is provided. The method comprises introducing a substance of interest into a detector. The detector includes an inlet configured to receive a substance of interest. The inlet includes a gas hole pattern. The method also comprises introducing a carrier gas into the detector. The carrier gas travels through the gas hole pattern and creates a gas curtain at the detector inlet. The gas curtain impedes atmospheric air from entering the detector through the detector inlet.

In another aspect of the present disclosure, a method of creating a gas curtain at an inlet for a detector of a substance of interest is provided. The method comprises introducing a substance of interest into a thermal desorber. The desorber includes an inlet configured to receive a substance of interest and an outlet in communication with the inlet. The inlet includes a gas hole pattern. The method further comprises heating the substance of interest. The method also comprises introducing a carrier gas into the desorber. The carrier gas travels through the gas hole pattern and creates a gas curtain at the desorber inlet. The gas curtain impedes atmospheric air from entering the desorber through the desorber inlet. The method further comprises transferring the substance of interest from the desorber to a detector.

In yet another aspect of the present disclosure, a thermal desorber is provided. The desorber includes an outlet and at least one plate configured to form an inlet that is configured to receive a substance of interest. The inlet includes a gas hole pattern. The at least one plate includes at least one inlet port configured to receive a carrier gas. The outlet is in communication with the inlet.

DETAILED DESCRIPTION OF THE DISCLOSURE

Figure 1:
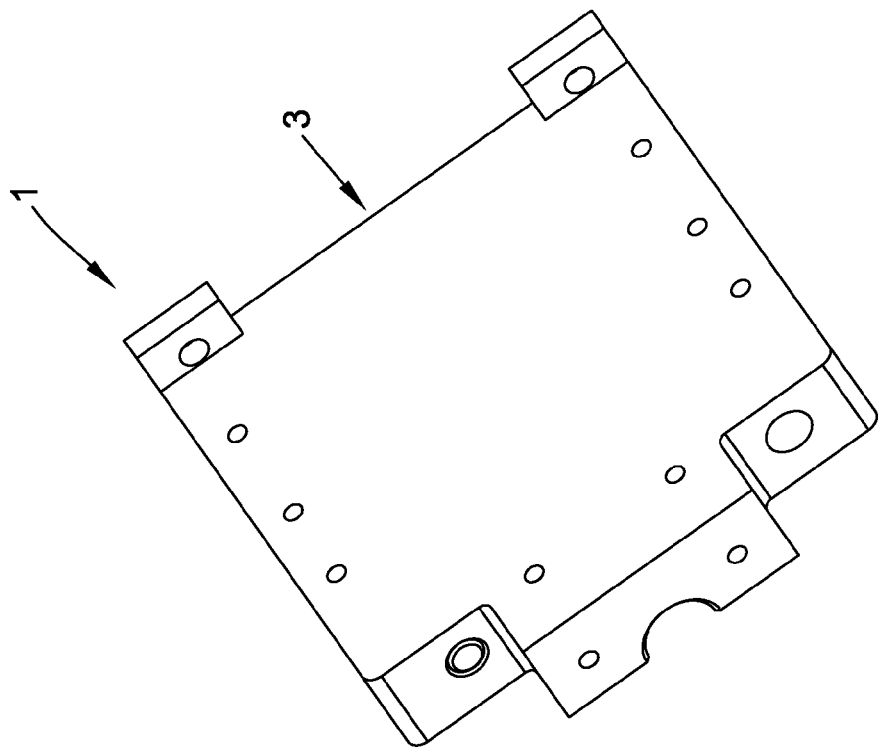
FIG. 1 is an exemplary embodiment of a desorber plate in accordance with the present disclosure.
Figure 1:
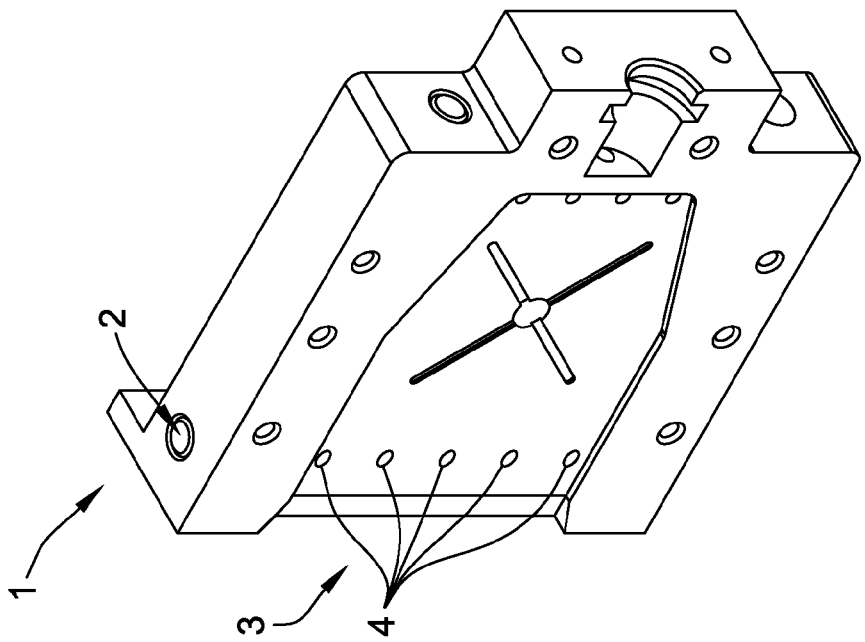

The present disclosure is directed to a method of creating a gas curtain inlet for a detector of a substance of interest. By creating a gas curtain inlet, the present disclosure provides a novel method to introduce clean, dried and/or doped air into an inlet and block out and/or impede atmospheric air from entering the inlet without having to make the inlet a sealed system. The methods disclosed herein simplify the inlet design, lower manufacturing costs compared to sealed inlet designs and provide improved performance over open-inlet designs because moist, contaminated air from the ambient atmosphere is not used as the carrier gas.

In one aspect of the present disclosure, a method of creating a gas curtain at an inlet for a detector of a substance of interest is provided. The method comprises introducing a substance of interest into a detector. The detector includes an inlet configured to receive a substance of interest. The inlet includes a gas hole pattern. The method also comprises introducing a carrier gas into the detector. The carrier gas travels through the gas hole pattern and creates a gas curtain at the detector inlet. The gas curtain impedes atmospheric air from entering the detector through the detector inlet.

In some embodiments, the carrier gas is introduced into the detector with a flow regime such that the carrier gas flow rate is about equal to or greater than a flow rate of the substance of interest (i.e., the flow rate of the sample being tested/detected). That is, in some embodiments, the carrier gas will be introduced into the detector at a flow rate greater than the flow rate of the substance of interest being introduced into the detector. In other embodiments, the carrier gas is introduced at a flow rate that is either equal to or slightly less than the flow rate of the substance of interest. In either instance, the flow regime creates a gas curtain at the opening of the inlet, which prevents and/or impedes atmospheric air from entering the detector. The substance of interest is then more accurately detected as a result of the gas curtain at the inlet of the detector.

In some embodiments, the carrier gas is introduced into the detector at a flow rate of from about 0 to about 10 liters per minute. In other embodiments, the carrier gas is introduced into the detector at a flow rate of from about 2 to about 8 liters per minute, or from about 4 to about 6 liters per minute. In some embodiments, the substance of interest is introduced into the detector at a flow rate that is lower than the flow rate of the carrier gas. In other embodiments, the substance of interest is introduced into the detector at a flow rate equal to the flow rate of the carrier gas. In yet other embodiments, the substance of interest is introduced into the detector at a flow rate that is from about 10% to about 20% greater than (i.e., faster than) the flow rate of the carrier gas.

The gas curtain inlet will impede atmospheric air from entering the detector through the inlet. In some embodiments, the gas curtain inlet will completely prevent atmospheric air from entering the detector. In other instances, the gas curtain inlet allows a minimal amount of atmospheric air to enter the detector. Thus, as used herein, the term "impede" includes both preventing all atmospheric air from entering the inlet and blocking the majority of atmospheric air from entering the inlet while allowing a de minimis amount of atmospheric air into the inlet.

In some embodiments, the carrier gas includes at least one of air, hydrogen, a noble gas, oxygen, nitrogen and carbon dioxide. In some embodiments, the air is prepared through drying and scrubbing before it is introduced into the detector. The air is cleaned, for example, through pumping the air through a pump and using a desiccant to remove moisture from the air.

The gas hole pattern of the present disclosure comprises at least one hole, at least two holes, at least three holes, at least four holes, or at least five holes. In some embodiments, the gas hole pattern consists of a single hole. In other embodiments, the gas hole pattern consists of five holes. In some embodiments, the gas hole pattern is located at or near the inlet. The hole or holes are optimally positioned to distribute the carrier gas flow evenly across the inlet opening to impede and/or block out atmospheric air while simultaneously covering the entire surface of the area of the substance of interest on, for example, a sample coupon. In some embodiments, the hole or holes are angled at the inlet.

In some embodiments, the carrier gas includes at least one of a dopant, a calibrant, a verification compound and a chemical modifier. In some embodiments, the carrier gas includes at least one of toluene, anisole, acetone, methyl salicylate, 2,6-di-tert-butyl-pyridine, 2,4-dimethylpyridine, 5-nitrovanillin, nicotinamide, isobutyramide, dichloromethane, ammonium carbamate, ammonia, hexachloroethane, 4-nitrobenzonitrile, a hydrocarbon, a partially or fully fluorinated, chlorinated, brominated or iodinated hydrocarbon, chlorine, ionizable compounds and substituted aliphatic or aromatic compounds. In some embodiments, the carrier gas includes toluene. In some embodiments, the at least one dopant, calibrant, verification compound and chemical modifier is introduced into the carrier gas at a flow rate of from about 10 ng/min to about 1 mg/min. A benefit of adding a dopant, calibrant, verification compound and/or chemical modifier at the inlet as part of the carrier gas is the elimination of the need to treat the gas down the line in the detection process, which further dilutes the substance of interest, and, as a result, lowers the detection sensitivity.

The substance of interest is any substance that a person having ordinary skill in the art is attempting to detect in accordance with the present disclosure. In some embodiments, the substance of interest includes at least one of an explosive, an energetic material, a taggant, a narcotic, a toxin, a chemical warfare agent, a biological warfare agent, a toxic industrial chemical, a toxic industrial material, and a pharmaceutical trace contaminant. In some embodiments, the explosive includes at least one of nitro, nitrate, triacetone triperoxide (TATP), ammonium nitrate (AN), ammonium nitrate fuel oil (ANFO), urea nitrate (UN), trinitrotoluene (TNT), ethylene glycol dinitrate (EGDN), nitroglycerin (NG), pentaerythritol tetranitrate (PE-TN), high melting explosive (HMX), Research Department Explosive (RDX) and black powder. In some embodiments, the narcotic includes at least one of cocaine, 3,4-methylenedioxy-N-methylamphetamine (MDMA), an opiate and diazepam.

In some embodiments, the detector of the present disclosure includes at least one of an ion mobility spectrometer (IMS), an ion trap mobility spectrometer (ITMS), a drift spectrometer (DS), a non-linear drift spectrometer, a field ion spectrometer (FIS), a radio frequency ion mobility increment spectrometer (IMIS), an ultra-high-field FAIMS, a differential ion mobility spectrometer (DIMS) and a differential mobility spectrometer (DMS), a field asymmetric ion mobility spectrometer (FAIMS), a traveling wave ion mobility spectrometer, a mass spectrometer (MS), a gas chromatograph (GC), an electron capture detector, a photoionization detector, a chemiluminescence-based detector, an electrochemical sensor, a semiconductor gas sensor, a raman spectrometer, a laser diode detector, an infrared spectrometer and a lab-on-a-chip detector. In some embodiments, a combination of detectors is used to detect the substance of interest.

The present disclosure is also directed to a thermal desorber. In some embodiments, the thermal desorber comprises an outlet and at least one plate configured to form an inlet. The inlet is configured to receive a substance of interest and includes a gas hole pattern. The at least one plate includes at least one inlet port configured to receive a carrier gas. The outlet is in communication with the inlet.

The thermal desorber, in some embodiments, comprises one plate, two plates, or more than two plates. In some embodiments, the thermal desorber comprises two or more plates. In other embodiments, the thermal desorber consists of a single plate. The single plate is manufactured by a plurality of methods known by persons having ordinary skill in the art, such as, but not limited to, welding, brazing, casting, milling and bonding. In yet other embodiments, the desorber consists of two plates. In any instance, whether the desorber is made of one, two, or two or more plates, the plate(s) are configured to form a desorber inlet.

In some embodiments, the desorber includes at least one inlet port. In some embodiments, the desorber includes multiple inlet ports. For example, in some embodiments the desorber has an inlet port located on each plate. In some embodiments, the desorber includes an inlet port on each side of each plate.

The desorber comprises a plenum in some embodiments. When the desorber does not comprise a plenum, in some embodiments the carrier gas is introduced directly into the desorber through the gas hole pattern. In some embodiments, however, the desorber comprises at least one of an integrated plenum and an external plenum. When a plenum is present, the carrier gas travels through the plenum and then through the gas hole pattern and into the desorber. In some embodiments, the gas hole pattern is located on the plenum. In some embodiments, the gas hole pattern comprises holes that are located at an angle on the plenum. When an integrated plenum is present within the desorber plate, in some embodiments, the internal volume of air entering the plenum is preheated as a result of the desorber plate or plates being held at a steady state desorption temperature. The integrated plenum connects the flow within such that, if present, only two side inlet ports are necessary.

Figure 2:
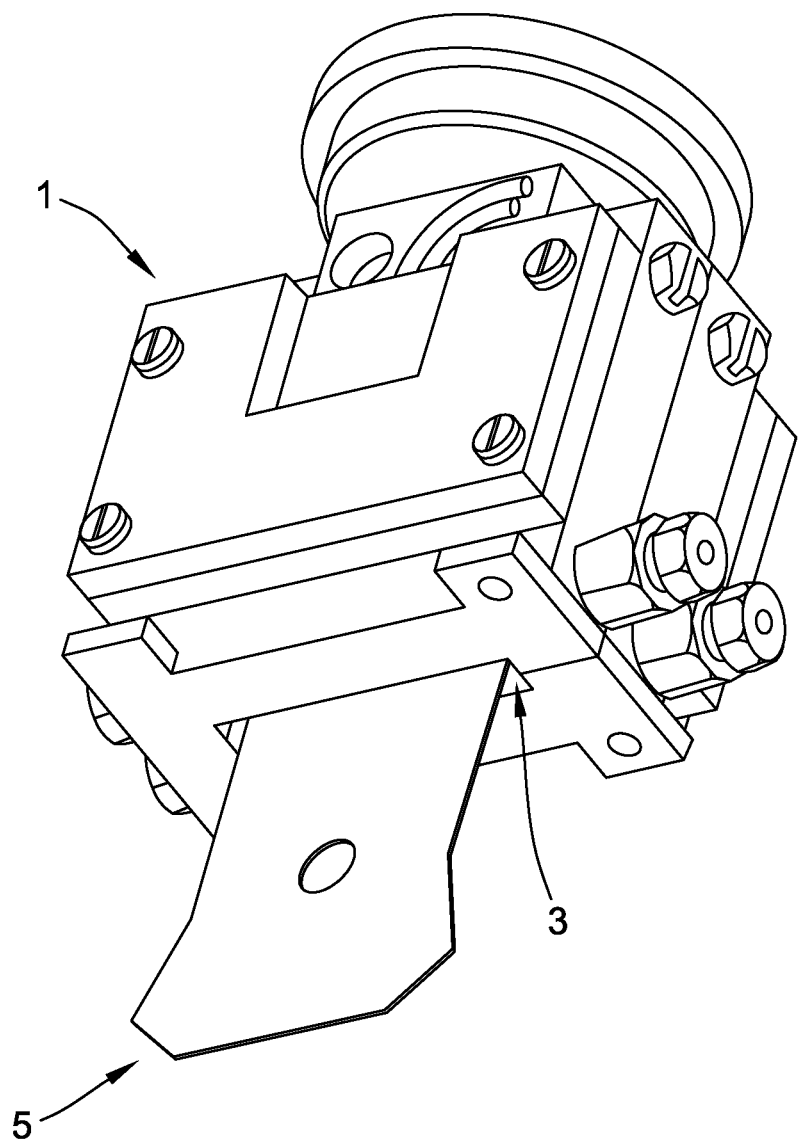
FIG. 2 is an exemplary embodiment of an integrated desorber with heater plates in accordance with the present disclosure.

FIG. 1 depicts an exemplary embodiment of a desorber in accordance with the present disclosure. The desorber 1 is shown as separated into two halves, such, as, for example, a desorber plate or plates. The desorber 1 comprises a plenum 2 and an inlet 3. A gas hole pattern 4 is located at the inlet 3. As shown in FIG. 2, the desorber 1 includes an inlet 3 for introduction of the substance of interest on a collection device 5. In some embodiments, the collection device 5 is, for example, a swab, a sample coupon, a preconcentrator device, and other devices known in the industry for collecting samples.

In yet another aspect of the present disclosure, a method of creating a gas curtain at an inlet for a detector of a substance of interest is provided. The method comprises introducing a substance of interest into a thermal desorber. The desorber includes an inlet configured to receive a substance of interest and an outlet in communication with the inlet. The inlet includes a gas hole pattern. The method further comprises heating the substance of interest. The method also comprises introducing a carrier gas into the desorber. The carrier gas travels through the gas hole pattern and creates a gas curtain at the desorber inlet. The gas curtain impedes atmospheric air from entering the desorber through the desorber inlet. The method further comprises transferring the substance of interest from the desorber to a detector.

The carrier gas, in some embodiments, is introduced into the desorber with a flow regime such that the carrier gas flow rate is about equal to or greater than a flow rate of the substance of interest. That is, in some embodiments the carrier gas will be introduced into the desorber at a flow rate greater than the flow rate of the substance of interest being introduced into the desorber. In other embodiments, the carrier gas is introduced at a flow rate that is either equal to or slightly less than the flow rate of the substance of interest. In either instance, the flow regime creates a gas curtain at the opening of the inlet, which prevents and/or impedes atmospheric air from entering the desorber.

In some embodiments, the carrier gas is introduced into the desorber at a flow rate of from about 0 to about 10 liters per minute. In other embodiments, the carrier gas is introduced into the desorber at a flow rate of from about 2 to about 8 liters per minute, or from about 4 to about 6 liters per minute. In some embodiments, the substance of interest is introduced into the desorber at a flow rate that is lower than the flow rate of the carrier gas. In other embodiments, the substance of interest is introduced into the desorber at a flow rate equal to the flow rate of the carrier gas. In yet other embodiments, the substance of interest is introduced into the desorber at a flow rate that is from about 10% to about 20% greater than (i.e., faster than) the flow rate of the carrier gas.

In some embodiments, the carrier gas includes at least one of air, hydrogen, a noble gas, nitrogen, oxygen and carbon dioxide. In some embodiments, the air is prepared through drying and scrubbing before it is introduced into the desorber. The air is cleaned, for example, through pumping the air through a pump and using a desiccant to remove moisture from the air. In some embodiments, the carrier gas is preheated before entering the desorber.

Figure 5A:
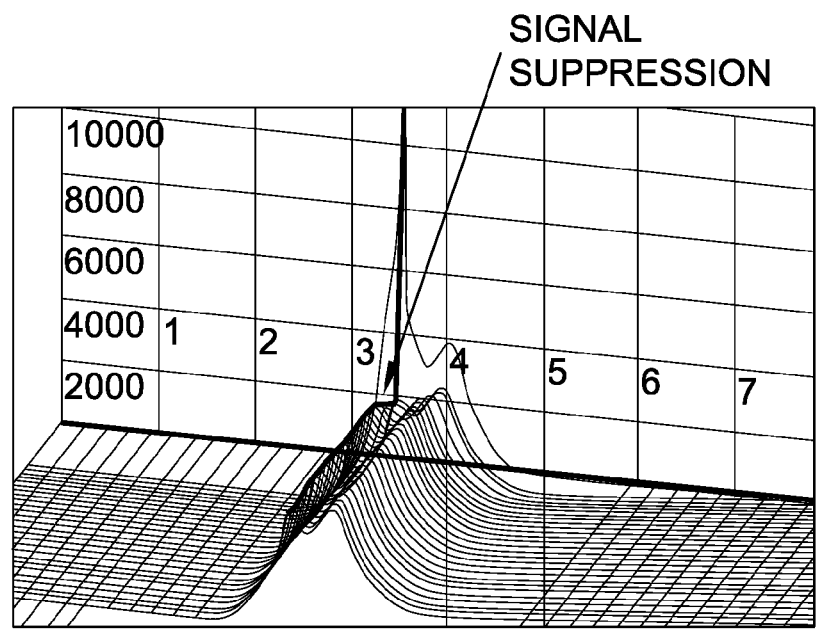
FIG. 5A is an exemplary embodiment of the signal suppression of a reactant ion peak (RIP) when an inlet is open to atmospheric air.
Figure 5B:
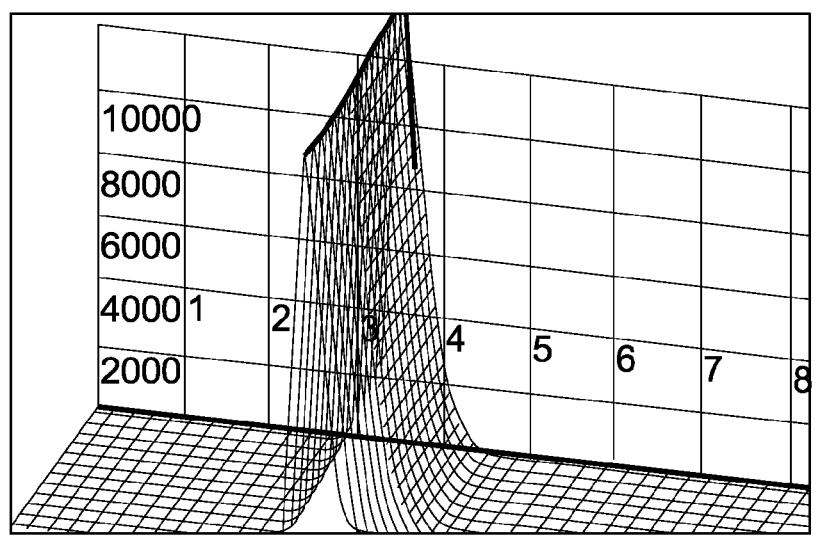
FIG. 5B is an exemplary embodiment of a reactant ion peak signal when atmospheric air is prevented from entering the detector.

The gas hole pattern of the present disclosure comprises at least one hole, at least two holes, at least three holes, at least four holes, or at least five holes. In some embodiments, the gas hole pattern consists of a single hole. In other embodiments, the gas hole pattern consists of five holes. In some embodiments, the gas hole pattern is located at or near the desorber inlet. The hole or holes are optimally positioned to distribute the carrier gas flow evenly across the inlet opening to impede and/or block out atmospheric air while simultaneously covering the entire surface area of the substance of interest on, for example, a sample coupon. In some embodiments, the hole or holes are angled at the inlet.

In some embodiments, the desorber includes an integrated plenum and the gas hole pattern is located within the plenum. In these embodiments, the carrier gas travels through the integrated plenum and then through the gas hole pattern and into the desorber. In some embodiments, the gas hole pattern is configured such that the hole or holes are angled on the plenum.

In some embodiments, a pump is used to facilitate transfer of the substance of interest from the desorber into the detector.

Thus, in an exemplary embodiment, trace illicit substances such as explosives, energetic materials, taggants, toxins, biological warfare agents, toxic industrial materials, pharmaceutical trace contaminants, narcotics, chemical warfare agents and toxic industrial chemicals are harvested off of a suspected surface by methods known in the art using, for example, a swab or vapor collection on a preconcentrator device. The swab or preconcentrator is then inserted into a thermal desorber located at the front end of a detector. The heat from the desorber changes the phase of the trace substance from solid to vapor, or releases the trapped vapor. The vapor is then pulled or pushed into a detector by a sampling pump. The back end of the detection system comprises a single, parallel or tandem of detectors. The carrier gas flow rate is modulated by the gas hole pattern to achieve a uniform flow across the sample trap area, such that minimal to no moist atmospheric air enters the desorber inlet and the substance of interest is effectively transported into the detector. The substance of interest is then more accurately detected as a result of the gas curtain at the inlet of the desorber.

In another aspect, a system for the detection of a substance of interest is provided. The system comprises a thermal desorber, a detector and a pump as defined elsewhere in this disclosure. FIG. 8 discloses an exemplary system in accordance with the present disclosure. The system comprises a desorber 1, a detector 6 and a pump 7, wherein the desorber 1 includes an inlet 3.

EXAMPLES

The following examples describe or illustrate various embodiments of the present disclosure. Other embodiments within the scope of the appended claims will be apparent to a skilled artisan considering the specification or practice of the disclosure as described herein. It is intended that the specification, together with the Examples, be considered exemplary only, with the scope and spirit of the disclosure being indicated by the claims, which follow the Examples.

Example 1

Example 1 examined the effect of signal suppression when atmospheric air is present in a detector. A blank run was conducted on the effect of atmospheric air on a detector's signal and is depicted in FIGS. 5A and 5B. FIG. 5A depicts a graph that illustrates how the detector's signal intensity is reduced when the inlet is left completely open to atmospheric air. FIG. 5B depicts a graph that illustrates the intensity of the signal when the inlet is blocked and atmospheric air does not enter the detector. Both FIGS. 5A and 5B depict blank runs that did not include any carrier gas or gas hole pattern. As shown from the blank runs, the detector's signal is significantly suppressed when the detector inlet is left open to atmospheric air, which makes it more difficult to detect a particular substance of interest.

Figure 6A:
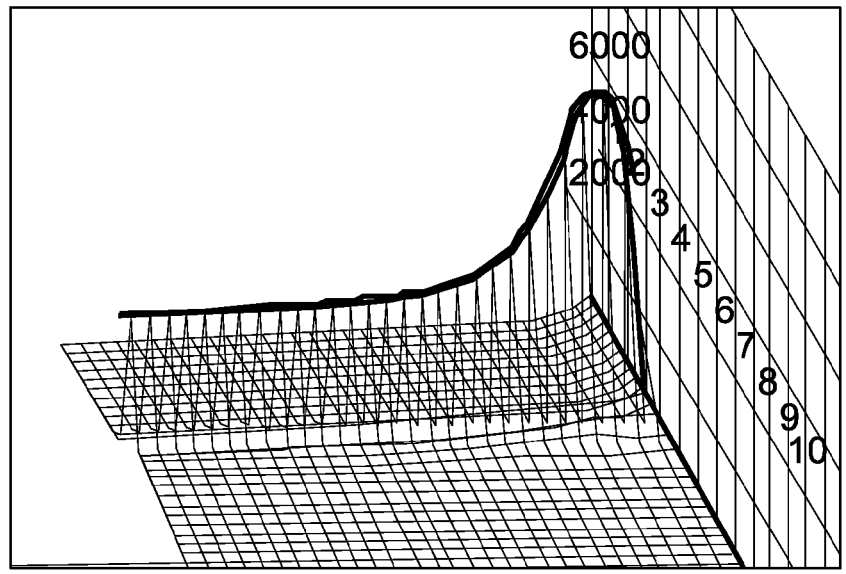
FIG. 6A is an exemplary embodiment of the reactant ion peak signal when an inlet is open to atmospheric air in accordance with the present disclosure.
Figure 6B:
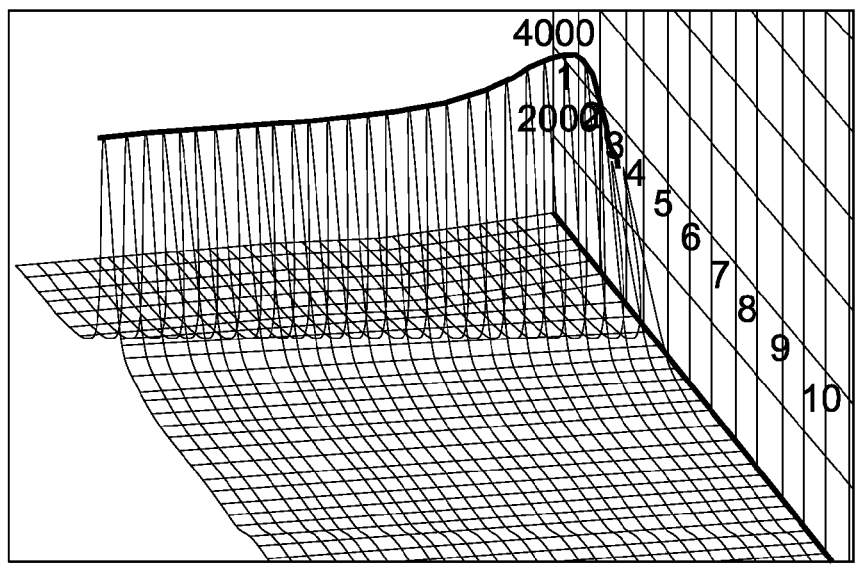
FIG. 6B is an exemplary embodiment of the reactant ion peak signal when a gas curtain in accordance with the present disclosure is applied at the inlet.

A study was then conducted when a gas curtain in accordance with the present disclosure is present at the detector inlet. FIG. 6A depicts the signal of the reactant ion peak (RIP) when no clean, dried air is used as the carrier gas and the inlet is open to atmospheric air. FIG. 6B depicts an exemplary embodiment of the RIP signal when clean, dried air was used as the carrier gas and was doped with toluene. The doped carrier gas was then introduced into the detector through a gas hole pattern and, as shown in FIG. 6B, the gas curtain inlet that is created as a result impedes atmospheric air from entering the detector and the detector signal has minimal, if any, depletion. Thus, Example 1 demonstrates the effectiveness of having the gas curtain present at the detector inlet.

Example 2

Figure 3:
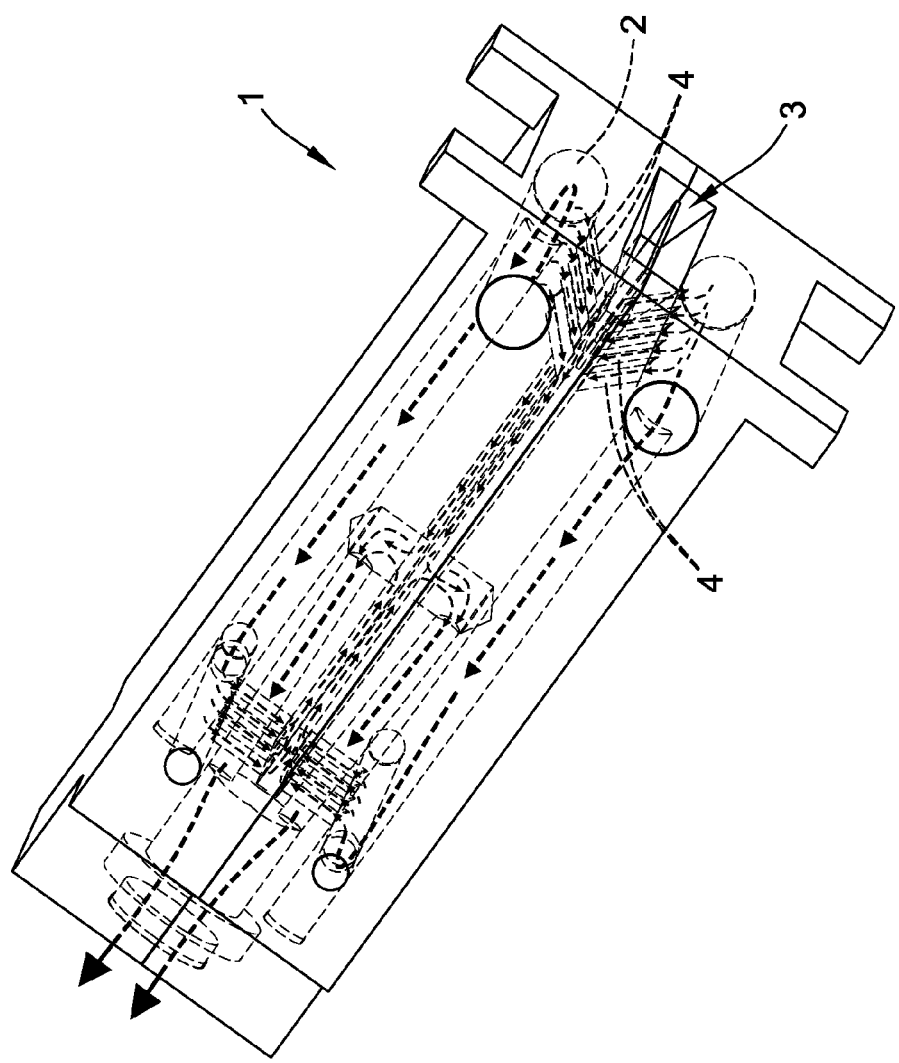
FIG. 3 is an exemplary embodiment of a hidden wire frame side view of an integrated desorber depicting flow regimes in accordance with the present disclosure.

Example 2 examined flow uniformity at a desorber inlet 3 using a computational fluid dynamics (CFD) simulator. Testing was performed at different flow rates, hole sizes, separation distances of the holes and angles for the holes to arrive at an exemplary geometry design. FIG. 3 depicts the simulation results for an inlet 3 design for a desorber 1 with a gas curtain where atmospheric air is blocked out by a carrier gas comprising dried, clean air while the majority of the carrier gas sweeps over the entire sample trap surface carrying the substance of interest into the detector (shown by the directional arrows at the opposite end of the inlet 3). The desorber 1 in FIG. 3 includes an integrated plenum 2 and a gas hole pattern 4 wherein the holes are located at an angle on the plenum 2. As shown in FIG. 3, the gas hole pattern 4 creates a uniform flow of the carrier gas across the sample trap area (depicted by arrows). As shown in FIG. 3, the carrier gas traveling through the plenum 2 and the gas hole pattern 4 creates the gas curtain at the inlet 3, which impedes atmospheric air from entering the desorber 1.

Figure 4:
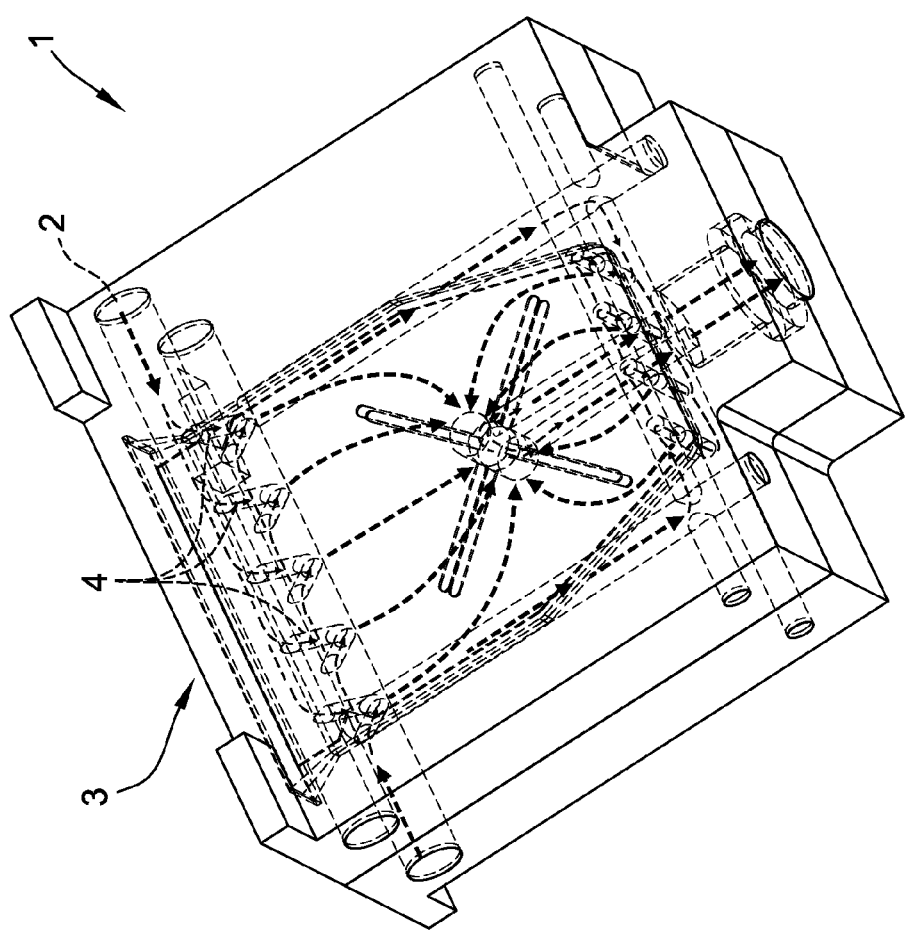
FIG. 4 is an exemplary embodiment of a hidden wire frame isometric view of a desorber with an integrated plenum depicting flow regimes in accordance with the present disclosure.

FIG. 4 is a different view of the same simulation tested in FIG. 3. FIG. 4 depicts a desorber 1 comprising an integrated plenum 2 and a gas hole pattern 4 that creates the gas curtain at the inlet 3 and impedes atmospheric air from entering the desorber while the substance of interest travels into the detector (shown by the directional arrows at the opposite end of the inlet 3). As seen in FIG. 4, the gas hole pattern 4 creates a uniform flow of the carrier gas across the sample trap area (depicted by arrows) and no, to minimal atmospheric air was found in the sample flow.

Example 3

Figure 7:
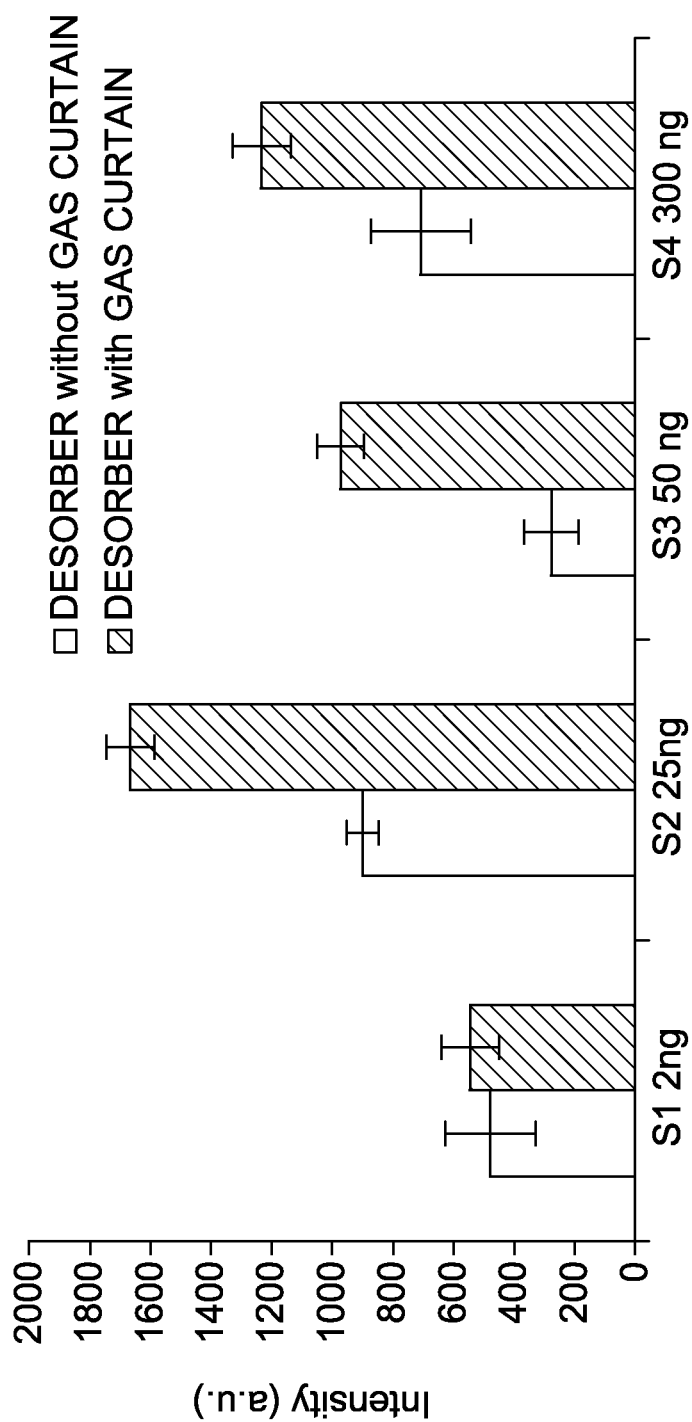
FIG. 7 is an exemplary embodiment of the signal intensity representing the analyte sensitivity with and without a gas curtain present at the desorber inlet in accordance with the present disclosure.
Figure 8:
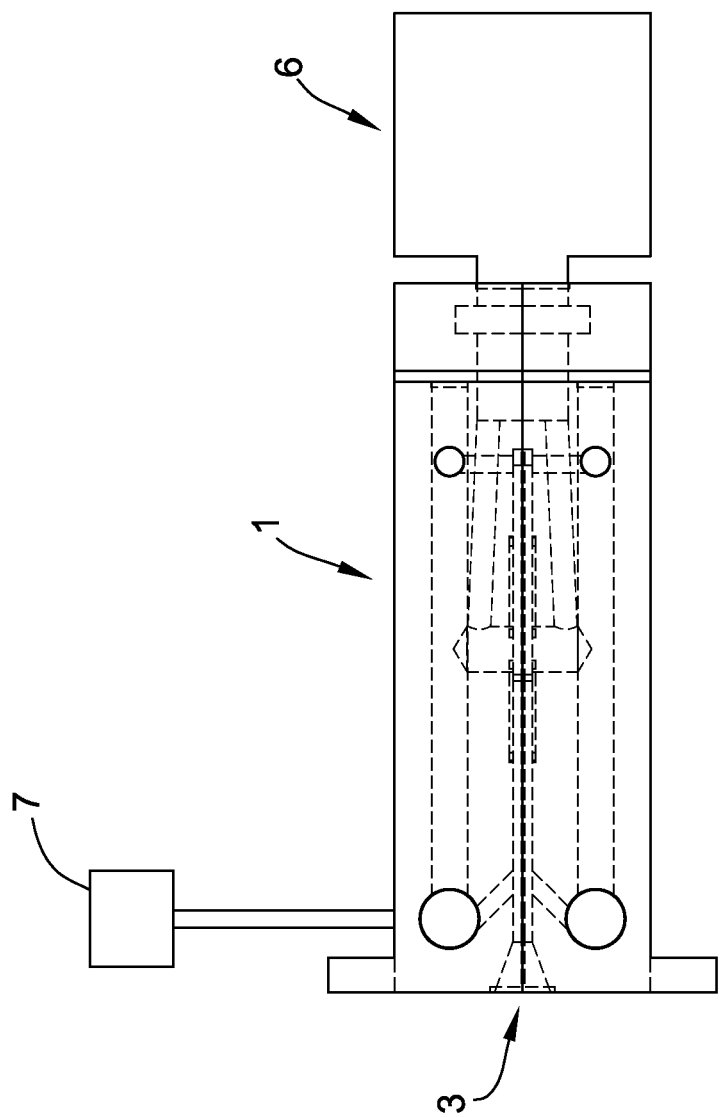
FIG. 8 is an exemplary embodiment of a system for the detection of a substance of interest in accordance with the present disclosure.

Example 3 tested a desorber with a gas curtain at the inlet and a desorber without a gas curtain at the inlet. Four substances of interest were analyzed through the desorber for the testing: (1) S1—PETN; (2) S2—Nitro; (3) S3—Nitrate; and, (4) S4—TATP. Dried, clean air was used as the carrier gas and was doped with toluene and ammonium carbamate. As shown in FIG. 7, for each substance of interest, when the gas curtain was present at the inlet, the desorber provided improved results in the form of a signal intensity increase. Thus, the gas curtain at the desorber inlet provided for faster reactant ion peak (RIP) recovery, increased sampling throughput, and lowered and controlled the moisture levels within the detection system, which resulted in higher analyte (i.e., substance of interest) sensitivity as shown in FIG. 7.

In accordance with the systems and methods of the present disclosure, Examples 1-3 show that when a gas curtain is present at an inlet of either a desorber or detector, atmospheric air is blocked and/or impeded from entering into the desorber or detector, and, as a result, the detection systems exhibited improved performance.

Exemplary embodiments of substance detection systems for determining the presence of substances of interest, and methods of operating such systems are not limited to the specific embodiments described herein, but rather, components of systems and/or steps of the methods may be utilized independently and separately from other components and/or steps described herein. For example, the methods may also be used in combination with other systems requiring determining the presence of substances of interest, and are not limited to practice with only the substance detection systems and methods as described herein. Rather, the exemplary embodiment can be implemented and utilized in connection with many other substance detection applications that are currently configured to determine the presence of substances of interest.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

Some embodiments involve the use of one or more electronic or computing devices. Such devices typically include a processor or controller, such as a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term processor.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:
1. A method of creating a gas curtain at an inlet for a detector of a substance of interest, the method comprising:
introducing a substance of interest into a detector, wherein the detector includes an inlet configured to receive a substance of interest, and the inlet includes a gas hole pattern comprising one or more holes located at an angle on said inlet; and, introducing a carrier gas into the detector, wherein the carrier gas travels through the gas hole pattern and creates a gas curtain at the detector inlet that impedes atmospheric air from entering the detector through the detector inlet.

2. The method of claim 1, wherein the carrier gas is introduced into the detector at a flow rate of from about 0 to about 10 liters per minute.

3. The method of claim 1, wherein the carrier gas is introduced into the detector at a flow rate that is about equal to or greater than a flow rate of the substance of interest.

4. The method of claim 1, wherein the carrier gas includes at least one of air, hydrogen, oxygen, a noble gas, nitrogen and carbon dioxide.

5. The method of claim 1, wherein the carrier gas includes at least one of a dopant, a calibrant, a verification compound and a chemical modifier.

6. The method of claim 5, wherein the carrier gas includes at least one of toluene, anisole, acetone, methyl salicylate, 2,6-di-tert-butyl-pyridine, 2,4-dimethylpyridine, 5-nitrovanillin, nicotinamide, isobutyramide, dichloromethane, ammonium carbamate, ammonia, hexachloroethane, 4-nitrobenzonitrile, a hydrocarbon, a partially or fully fluorinated, chlorinated, brominated or iodinated hydrocarbon, chlorine, ionizable compounds and substituted aliphatic or aromatic compounds.

7. The method of claim 1, wherein the substance of interest includes at least one of an explosive, an energetic material, a taggant, a narcotic, a toxin, a chemical warfare agent, a biological warfare agent, a toxic industrial chemical, a toxic industrial material and a pharmaceutical trace contaminant.

8. The method of claim 1, wherein the detector includes at least one of an ion mobility spectrometer (IMS), an ion trap mobility spectrometer (ITMS), a drift spectrometer (DS), a non-linear drift spectrometer, a field ion spectrometer (FIS), a radio frequency ion mobility increment spectrometer (IMIS), a field asymmetric ion mobility spectrometer (FAIMS), an ultra-high-field FAIMS, a differential ion mobility spectrometer (DIMS) and a differential mobility spectrometer (DMS), a traveling wave ion mobility spectrometer, a semiconductor gas sensor, a raman spectrometer, a laser diode detector, a mass spectrometer (MS), a gas chromatograph (GC), an electron capture detector, a photoionization detector, a chemiluminescence-based detector, an electrochemical sensor, an infrared spectrometer and a lab-on-a-chip detector.

9. A method of creating a gas curtain at an inlet for a detector of a substance of interest, the method comprising:

introducing a substance of interest into a thermal desorber, wherein the desorber includes an inlet configured to receive a substance of interest and an outlet in communication with the inlet, wherein the inlet includes a gas hole pattern comprising one or more holes located at an angle on said inlet;

heating the substance of interest;

introducing a carrier gas into the desorber, wherein the carrier gas travels through the gas hole pattern and creates a gas curtain at the desorber inlet that impedes atmospheric air from entering the desorber through the desorber inlet; and, transferring the substance of interest from the desorber to a detector.

10. The method of claim 9, wherein the carrier gas is introduced into the desorber at a flow rate about equal to or greater than a flow rate of the substance of interest.

11. The method of claim 9, wherein the carrier gas includes at least one of air, hydrogen, oxygen, a noble gas, nitrogen and carbon dioxide.

12. The method of claim 9, wherein the carrier gas includes at least one of a dopant, a calibrant, a verification compound and a chemical modifier.

13. The method of claim 12, wherein the carrier gas includes at least one of toluene, anisole, acetone, methyl salicylate, 2,6-di-tert-butyl-pyridine, 2,4-dimethylpyridine, 5-nitrovanillin, nicotinamide, isobutyramide, dichloromethane, ammonium carbamate, ammonia, hexachloroethane, 4-nitrobenzonitrile, a hydrocarbon, a partially or fully fluorinated, chlorinated, brominated or iodinated hydrocarbon, chlorine, ionizable compounds and substituted aliphatic or aromatic compounds.

14. The method of claim 9, wherein the desorber includes at least one of an integrated plenum and an external plenum.

15. The method of claim 9, wherein the gas hole pattern consists of a single hole.

16. A thermal desorber comprising:

an outlet and at least one plate configured to form an inlet that is configured to receive a substance of interest, wherein said at least one plate includes at least one of an integrated plenum and an external plenum, wherein the inlet includes a gas hole pattern comprising one or more holes that are located at an angle on said plenum, wherein said at least one plate includes at least one inlet port configured to receive a carrier gas, and wherein said outlet is in communication with said inlet.

17. The desorber of claim 16, wherein said desorber consists of a single plate.

18. The desorber of claim 16, wherein said gas hole pattern consists of a single hole.

* * * * *